US008859624B2

(12) United States Patent
Lin et al.

(10) Patent No.: US 8,859,624 B2
(45) Date of Patent: Oct. 14, 2014

(54) STABLE RASAGILINE COMPOSITION

(75) Inventors: Jialiang Lin, Chongqing (CN); Jie Deng, Chongqing (CN); Hao Chen, Chongqing (CN); Tao Zhang, Chongqing (CN)

(73) Assignee: Chongqing Pharmaceutical Research Institute Co., Ltd., Chongqing (CN)

( * ) Notice: Subject to any disclaimer, the term of this patent is extended or adjusted under 35 U.S.C. 154(b) by 0 days.

(21) Appl. No.: 13/504,178

(22) PCT Filed: Oct. 28, 2010

(86) PCT No.: PCT/CN2010/078189
§ 371 (c)(1),
(2), (4) Date: Apr. 26, 2012

(87) PCT Pub. No.: WO2011/050728
PCT Pub. Date: May 5, 2011

(65) Prior Publication Data
US 2012/0214877 A1 Aug. 23, 2012

(30) Foreign Application Priority Data
Oct. 29, 2009 (CN) .......................... 2009 1 0191252

(51) Int. Cl.
*A01N 33/02* (2006.01)
*A61K 31/135* (2006.01)
*A61F 13/00* (2006.01)
*A61K 9/70* (2006.01)
*A61K 31/355* (2006.01)
*A61K 47/22* (2006.01)
*A61K 9/00* (2006.01)
*A61K 47/10* (2006.01)
*A61K 9/06* (2006.01)
*A61K 31/375* (2006.01)

(52) U.S. Cl.
CPC ............. *A61K 31/135* (2013.01); *A61K 31/355* (2013.01); *A61K 9/7069* (2013.01); *A61K 47/22* (2013.01); *A61K 9/7061* (2013.01); *A61K 9/0014* (2013.01); *A61K 47/10* (2013.01); *A61K 9/06* (2013.01); *A61K 31/375* (2013.01)
USPC ......................................... 514/657; 424/449

(58) Field of Classification Search
USPC ........................................ 514/657; 424/449
See application file for complete search history.

(56) References Cited

U.S. PATENT DOCUMENTS

| 7,220,473 B2 * | 5/2007 | Beier et al. .................... 428/40.2 |
| 2004/0034083 A1 * | 2/2004 | Stephenson et al. ........... 514/406 |
| 2007/0287796 A1 * | 12/2007 | Ashtekar et al. ............... 524/769 |
| 2009/0062400 A1 * | 3/2009 | Oron et al. ..................... 514/657 |

FOREIGN PATENT DOCUMENTS

| CA | 2 727 149 | 12/2009 |
| CN | 1178461 | 4/1998 |
| CN | 1911211 | 2/2007 |
| CN | 101032474 | 9/2007 |
| CN | 101606923 | 12/2009 |
| EP | 2 011 488 | 1/2009 |
| JP | 10-506409 | 6/1998 |
| JP | 2006-522800 | 10/2006 |
| JP | 2009-529011 | 8/2009 |
| JP | 2011-524353 | 9/2011 |
| JP | 2011-524907 | 9/2011 |
| JP | 2011-525489 | 9/2011 |
| JP | 2012-515775 | 7/2012 |
| WO | WO 2008/076348 | 6/2008 |
| WO | WO 2009/151594 | 12/2009 |
| WO | WO 2009/152777 | 12/2009 |

OTHER PUBLICATIONS

Ebadi et al (Progress in Neurobiology vol. 48, pp. 1 to 19, 1996).*
Extended European Search Report from European Application No. 10826091.0 mailed Feb. 4, 2013.
International Search Report (Form PCT/ISA/210) for corresponding International Application No. PCT/CN2010/078189.
Canadian Office Action for corresponding application No. 2,777,532 dated May 14, 2013.

* cited by examiner

*Primary Examiner* — Benjamin Packard
(74) *Attorney, Agent, or Firm* — Mercahnt & Gould P.C.

(57) ABSTRACT

The present invention provides a stable composition of rasagiline comprising an effective dosage of rasagiline or its pharmaceutically acceptable salts and an antioxidant used as a stabilizer. The dosage forms of the composition are pharmaceutically common transdermal-drug delivery dosage form and mucoadhesive delivery dosage form, such as patch, gel, ointment, cream, cataplasm, film, spray and solution, etc. The composition can be used to prevent or treat mental disorders.

12 Claims, No Drawings

STABLE RASAGILINE COMPOSITION

This application is a National Stage Application of PCT/CN2010/078189, filed 28 Oct. 2010, which claims benefit of Ser. No. 200910191252.6, filed 29 Oct. 2009 in China and which applications are incorporated herein by reference. To the extent appropriate, a claim of priority is made to each of the above disclosed applications.

FIELD OF THE INVENTION

The invention belongs to the field of pharmaceutical preparation, in particular relates to a stable rasagiline composition, comprising an effective amount of rasagiline or a pharmaceutically acceptable salt thereof and an antioxidant as a stabilizer. The composition is used for the treatment or prevention of mental system disease.

BACKGROUND OF THE INVENTION

Rasagiline is an irreversible selective monoamine oxidase B (MAOB) inhibitor, which can be used for the treatment or prevention of Parkinson's disease, Alzheimer's disease, depression, hyperkinetic syndrome of childhood, restless legs syndrome, multiple sclerosis and abstinence syndrome. The molecular structure of rasagiline is shown as below:

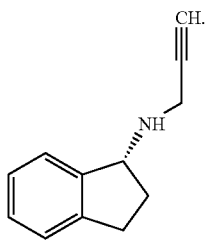 [SMILES: C#CCN[C@@H]1CCc2ccccc21]

Rasagiline has strong efficacy, and taking food after oral administration will result in a decrease of blood drug concentration by 60%, in addition, patients with Parkinson's disease have mobility impairments, so the hepatic first-pass effect can be avoided and more steady absorption will be achieved by preparing rasagiline into preparations being administerd by percutaneous and mucosal routes.

Dosage forms administered by percutaneous and mucosal routes include patch, cataplasm, gel, ointment, cream, film, spray, solution and the like. These dosage forms are administered by transdermal and mucosal routes and have their own characteristics: patch and cataplasm can be more firmly attached to the skin so that the drug is slowly and sustainedly released and absorbed, and are convenient to use without pollution to clothes. Gel, ointment, cream, spray and solution can be simply prepared. Film is commonly used for drugs absorbed by oral mucosa, and the drugs are absorbed faster and more complete, and the hepatic first-pass effect can also be avoided.

Chinese patent application CN101032474A discloses a transdermal patch of rasagiline for the treatment or prevention of mental system diseases, the patch comprises an inert support layer which will not chemically react with matrix components, a matrix layer comprising rasagiline or a pharmaceutically acceptable salt thereof and a protective layer to be removed prior to use. The matrix layer is a drug reservoir comprising an organic polymer material and an inorganic or organic material as a modulator, and the reservoir comprises rasagiline. The matrix layer also contains one or more substances that promote the transdermal absorption of rasagiline. In the examples, the pH of the patch maintains in an alkaline range (above 7.0). Although a good transdermal permeation effect could be achieved, it is found from study that the stability of the drug is not good under conditions of high temperature stability test, which may be unfavorable to long-term storage.

Chinese patent application No. CN200810069850.1 (Publication No. CN101606923A) discloses a stable transdermal patch of rasagiline released in a controllable manner comprising an effective amount of rasagiline and a pharmaceutically acceptable salt thereof and b) at least one hydrophilic polymer matrix, and c) the pH value of the patch is not greater than 7.0, preferably not less than 3.0 and not greater than 6.5. Although the patch could maintein the stability of rasagiline and good transdermal effect, and is suitable for long-term storage and is less irritative to the skin, it contains more hydrophilic polymer matrixes, thus, it is not sweat-proof and easy to fall off when being attached to the skin. If a combination of a hydrophilic polymer matrix and a non-hydrophilic polymer matrix is used to prepare a patch, the preparation steps are very complicated, the selection conditions for matrix material is very harsh, and the production cost is high.

Therefore, there is still a need for new rasagiline compositions to meet a variety of needs.

SUMMARY OF THE INVENTION

In one aspect, the present invention provides a stable rasagiline composition comprising rasagiline or a pharmaceutically acceptable salt thereof in combination with a pharmaceutically acceptable antioxidant. The composition has good stability under the experimental conditions of high temperature stability (60° C. for 10 days). If the composition is in the form of a patch, the matrixes are not hard to select and are easily available, moreover, the patch can be firmly attached to the skin and is not ready to fall off.

According to certain embodiments of the composition according to the present invention, the amount of the antioxidant is 0.01% to 1% based on the total weight of the composition.

According to certain embodiments of the composition according to the present invention, the amount of rasagiline or a pharmaceutically acceptable salt thereof is 0.1% to 40% based on the total weight of the composition.

According to certain embodiments of the composition according to the present invention, the pharmaceutically acceptable salts of rasagiline include hydrochloride, mesylate, ethyl sulfonate or sulfate. According to certain embodiments of the composition according to the present invention, rasagiline is preferably present in the form of free base.

According to certain embodiments of the composition according to the present invention, the antioxidant may be any suitable pharmaceutically acceptable antioxidant, for example, it can be one or more substances selected from the group consisting of tocopherol or an ester thereof, ascorbyl palmitate, ascorbic acid, butylated hydroxyl toluene (chemical name: 2,6-di-tert-butyl-4-methyl phenol, BHT), butylated hydroxy anisole (chemical name: 3-tert-butyl-4-methoxy phenol, BHA) or propyl gallate, citric acid or a salt thereof; preferably one or more selected from the group consisting of ascorbyl palmitate, ascorbic acid, butylated hydroxyl toluene, butylated hydroxy anisole or butylated hydroxy propyl gallate.

According to certain embodiments of the composition according to the present invention, the compositions are presented in the dosage form of transdermal or mucosal preparations. Said transdermal preparation is transdermal patch, cataplasm, emulsion, cream, spray or gel, preferably transdermal patch. Said mucosal preparation is film or spray.

According to certain embodiments of the composition according to the present invention, the composition further comprises one or more excipients (carriers) selected from the group consisting of polyacrylic acid polymers, silicone polymers, polyvinyl alcohol polymers, polyvinylpyrrolidone polymers, ethylene vinyl acetate copolymers, cellulose polymers, polyethylene glycol polymers, carbomer polymers, polyethyleneoxide polymers, gelatin, alginic acid or a salt thereof, tragacanth, arabic gum, silicone oil, water, ethanol, acetone, propanol, propylene glycol, glycerol, ethyl acetate, cetyl alcohol, stearyl alcohol, stearic acid, paraffin, beeswax, lanolin compounds, magnesium aluminum silicate, kaolin, titanium dioxide, zinc oxide, aluminum hydroxide, aluminum chloride, citric acid, tartaric acid, ethylene diamine tetraacetic acid (EDTA).

Suitable excipients (carriers) can be selected according to different dosage forms for the composition of the present invention depending on conventional technology and knowledge of corresponding preparations in the art. For a transdermal patch, the polymers such as polyacrylic acid polymers, silicone polymers or polymer materials mentioned above can be selected as a matrix, and then a suitable solvent such as ethyl acetate can be selected. These combinations of excipients selected can be understood by the skilled in the art based on conventional knowledge, for example those disclosed in CN101032474A (published on Sep. 12, 2007, the contents of which are incorporated herein by reference in its entirety).

According to certain embodiments of the composition according to the present invention, in addition to the antioxidants and excipients (carriers) mentioned above, the transdermal preparations further comprise a transdermal penetration enhancer. The transdermal penetration enhancer is one or more selected from azone, isopropyl myristate, oleic acid and menthol.

According to certain embodiments of the composition according to the present invention, rasagiline can be present in any type of carriers known in the art. One use of carriers is to prepare the drug into a patch, cataplasm, cream, gel and other drug dosage forms. Rasagiline can be present in one or more forms in the carriers, such as salt, free base, microcrystalline and amorphous forms, microemulsion, etc. Preferably, rasagiline exists in the form of free base.

According to certain embodiments of the composition according to the present invention, the carrier may contain one or more polymers. For a patch, polyacrylic acid polymers and silicone polymers are preferred. For a gel, ointment, cream, film, cataplasm and solution, polyacrylic acid polymers, polyvinyl alcohol polymers, polyvinylpyrrolidone polymers, ethylene vinyl acetate copolymers, cellulose polymers, polyethyleneglycol polymers, carbomer polymers, polyethylene oxide polymers, gelatin, alginic acid and salts thereof, tragacanth, arabic gum, silicone oil and the like are preferred.

According to certain embodiments of the composition according to the present invention, the carrier may contain one or more small molecular compounds, such as water, ethanol, acetone, propanol, propylene glycol, glycerol, ethyl acetate, medium and long chain aliphatic (C4-24) alcohol, such as cetyl alcohol/stearyl alcohol, stearic acid, paraffin, beewax, lanolin compounds, magnesium aluminum silicate, kaolin, titanium dioxide, zinc oxide, aluminum hydroxide, aluminum chloride, citric acid, tartaric acid, ethylene diamine tetraacetic acid (EDTA) etc.

According to certain embodiments of the composition according to the present invention, the compositions can also contain a skin penetration enhancer, such as azone, isopropyl myristate, oleic acid, menthol.

The preparation methods for various formulations of the compositions according to the present invention can be preformed by conventional manufacturing techniques in the art, such as those described in CN101032474A.

The composition in which an antioxidant is added according to the present invention exhibits a surprising stability, especially when the composition is prepared into a transdermal patch. Rasagiline in the transdermal patch is very stable, and the transdermal patch is attached to the skin and not easy to fall off, so the transdermal effect is good. Moreover, the selected matrix material is easily available, and the operation is convenient and suitable for industrialized production.

In another aspect, the invention provides the use of any composition mentioned-above in the preparation of a medicament for the treatment or prevention of mental system diseases. The stable pharmaceutical composition comprising rasagiline according to the present invention is used for the treatment or prevention of mental system diseases, such as Parkinson's disease, Alzheimer's disease, depression, hyperkinetic syndrome of childhood, restless legs syndrome, multiple sclerosis and abstinence syndrome, etc. The amount of the composition used is that ensures the plasma concentration achieves a therapeutically effective amount (effective blood drug concentration). The compositions can be administered once a day, or once every two to three days, or once a week.

DETAILED DESCRIPTION OF THE INVENTION

The examples according to the present invention are intended to further illustrate the present invention, but not to limit the scope of the present invention.

The percentage concentration of each component in the compositions in the examples is calculated based on the weight percent of the total weight of the composition (W/W).

EXAMPLE 1

A Transdermal Patch Comprising Rasagiline and Tocopherol as an Antioxidant

TABLE 1

The formula of the composition for a transdermal patch comprising rasagiline and tocopherol as an antioxidant

| | Composition 1-1 | Composition 1-2 | Composition 1-3 | Composition 1-4 |
|---|---|---|---|---|
| active pharma-ceutical ingredient | rasagiline, 10% | rasagiline, 10% | rasagiline, 10% | rasagiline, 10% |
| excipient | ethyl acetate, 49.95% polyacrylic acid polymer, 40% | ethyl acetate, 49.5% silicone polymer, 40% | ethyl acetate, 49% polyacrylic acid polymer, 20%, silicone polymer, 20% | ethyl acetate, 50% polyacrylic acid polymer, 20%, silicone polymer, 20% |
| anti-oxidant | tocopherol, 0.05% | tocopherol, 0.5% | tocopherol, 1% | — |

Preparation method: rasagiline (free base), the polymer and/or the antioxidant in the above table were added to ethyl acetate and mixed to get a sticky matrix. The matrix was coated on a 75 μm thin transparent PET layer (protective layer) to form a film in thickness of 0.2 mm. After being oven-dried at 60° C. for 5 minutes, the film was covered with a back lining made of polyethylene and then was transferred, and the patch was punched or cut into the final sheet.

Prior to application to the skin, the protective layer is removed.

Relevant substances: the so-called "relevant substances" refer to the (relevant) impurities produced by the decomposition of rasagiline during the preparation or storage of rasagiline composition that may adversely affect the human bodies, and the limitation amount thereof is need to be controlled. The impurity is usually not a single compoud, and it may be a homologue of the active pharmaceutical ingredient whose structure is temporarily not possible or convenient or necessary to be determined, thus, these substances are collectively called "related substances".

Determination of related substances: (1) preparation of the test solution: A suitable amount of sample containing 20 mg rasagiline was taken. After the protective layer was removed, the sample was placed in a 50 ml volumetric flask, then 25 ml of solution of 0.1 mol/L hydrochloric acid in methanol was added thereto. The resulting mixture was sonicated for 30 minutes, cooled and diluted with the mobile phase to volume. The mixture was shaken uniformly and then centrifuged at 4000 r/min for 10 minutes. The supernatant was taken and used as the test solution; (2) preparation of the control solution: 1.0 ml test solution was taken precisely and placed in a 100 ml volumetric flask, then diluted with the mobile phase to volume. The resulting mixture was shaken uniformly and used as the control solution; (3) determination method: 20 μl of the test solution and the control solution were taken precisely and injected into a liquid chromatograph respectively. The chromatograms were recorded. The related substances were calculated based on the self-control method of the main ingredient. The equation was as follows:

Content of the related substances=(the total peak area of the test solution−the main peak area of the test solution)×100%/(the main peak area of the control solution×100)

wherein, the total peak does not include the excipient peak and the solvent peak, and the main peak is rasagiline peak.

For the determination of the related substances using a high performance liquid chromatography, the mobile phase was a solution of perchloric acid in ammonia (pH=2.5)/acetonitrile and a gradient elution was used (the gradient elution condition was shown in Table 1). The flow rate was 1 ml/min, and the column was a Boston Crest ODS column. The column temperature was 25° C.

TABLE 1 the gradient elution condition employed in the determination of the related substances using a high performance liquid chromatography

| gradient time (min) | a solution of perchloric acid in ammonia (v/v) | acetonitrile (v/v) |
| --- | --- | --- |
| 0 | 80% | 20% |
| 15 | 80% | 20% |
| 35 | 65% | 35% |
| 50 | 80% | 20% |
| 55 | 80% | 20% |

The composition according to the present invention provides a more stable system at high temperature. For the patches of the compositions 1-1 to 1-4 according to Example 1, after being stored at 60° C. for 10 days, content of the related substances was determined, and the results were shown in Table 3. The results showed that content of the related substances of the patches with the antioxidant after storage was still less than 5%, while that of the related substances of the patches without the antioxidant was greater than 5%.

TABLE 3 content of the related substances of the composition according to Example 1

| storage conditions | content of the related substances of Composition 1-1 | content of the related substances of Composition 1-2 | content of the related substances of Composition 1-3 | content of the related substances of Composition 1-4 |
| --- | --- | --- | --- | --- |
| 0 day | 0.16% | 0.15% | 0.15% | 0.17% |
| 60° C., 5 days | 0.88% | 0.72% | 0.23% | 3.56% |
| 60° C., 10 days | 2.84% | 1.94% | 1.28% | 12.27% |

Falling-off and shift of patches: a 10 cm$^2$ patch was attached to the chest skin of six adult healthy male volunteers (aged 20 to 40 years) respectively, and the falling off and shift of the patches was observed for 3 consecutive days. The results were shown in Table 4.

TABLE 4 the falling-off and shift of the patch according to Example 1 and the patch disclosed in CN101606923A

| patch | falling-off | shift (more than 5 mm) |
| --- | --- | --- |
| Composition 1-1 | no | no |
| Composition 1-2 | no | no |
| Composition 1-3 | no | no |
| Example 3 in CN101606923A | 2 | 3 |
| Example 4 in CN101606923A | 1 | 3 |
| Example 5 in CN101606923A | 2 | 2 |
| Example 6 in CN101606923A | 2 | 2 |

It can be seen from Table 4 that the patch in Example 1 according to the present invention could maintain sufficient adhesion and did not fall off or shift, while the patches prepared in Examples 3, 4, 5 and 6 in CN101606923A had falling-off or shift phenomenon 3 days after being attached to human chest skin.

In addition, for the patches prepared according to Examples 1 and 2 in CN101606923A, rasagiline was reacted with methanesulfonic acid to form a mesylate whose solubility in a non-hydrophilic material was small and the drug loading of the patch was low. The cumulative penetration was significantly lower compared with the system provided by the present invention.

EXAMPLE 2

A Transdermal Patch Comprising Rasagiline and Butylated Hydroxy Toluene as an Antioxidant

TABLE 5

The formula of the composition for a transdermal patch comprising rasagiline and butylated hydroxy toluene as an antioxidant

|  | Composition 2-1 | Composition 2-2 | Composition 2-3 | Composition 2-4 |
|---|---|---|---|---|
| active pharmaceutical ingredient | rasagiline, 10% | rasagiline, 10% | rasagiline, 10% | rasagiline, 10% |
| solvent | ethyl acetate, 49.95% | ethyl acetate, 49.5% | ethyl acetate, 49% | ethyl acetate, 50% |
| polymer | polyacrylic acid polymer, 40% | silicone polymer, 40% | polyacrylic acid polymer, 20%, silicone polymer, 20% | polyacrylic acid polymer, 20%, silicone polymer, 20% |
| antioxidant | butylated hydroxy toluene, 0.05% | butylated hydroxy toluene, 0.5% | butylated hydroxy toluene, 1% | — |

Preparation method: the Active pharmaceutical ingredient, the polymer and/or the antioxidant in the formula were added to ethyl acetate and mixed to get a sticky matrix. The matrix was coated on a 75 μm thin transparent PET layer (protective layer) to form a film in thickness of 0.2 mm. After being oven-dried at 60° C. for 5 minutes, the film was covered with a back lining made of polyethylene and was transferred, and then the patch was punched or cut into final sheets.

Prior to application to the skin, the protective layer was removed.

The compositions according to the present invention provide a more stable release system (patch) at high temperature. After being stored at 60° C. for 10 days, the content of the related substances of the composition according to the present invention was less than 2%, while that of the related substances of the composition without the antioxidant was greater than 5%. The results were shown in Table 6.

TABLE 6 content of the related substances of the composition according to Example 2

| storage conditions | content of the related substances of Composition 2-1 | content of the related substances of Composition 2-2 | content of the related substances of Composition 2-3 | content of the related substances of Composition 2-4 |
|---|---|---|---|---|
| 0 day | 0.15% | 0.14% | 0.13% | 0.17% |
| 60° C., 5 days | 0.82% | 0.39% | 0.25% | 3.56% |
| 60° C., 10 days | 1.77% | 1.01% | 0.79% | 12.27% |

A 10 cm² of patch was attached to the skin of the chest of a human being, and the patches could maintain sufficient adhesion and no falling-off or shift occurred within 3 consecutive days.

EXAMPLE 3

A Transdermal Patch Comprising Rasagiline and Ascorbyl Palmitate as an Antioxidant

TABLE 7

The formula of the composition for a transdermal patch comprising rasagiline and ascorbyl palmitate as an antioxidant

|  | Composition 3-1 | Composition 3-2 | Composition 3-3 | Composition 3-4 |
|---|---|---|---|---|
| rasagiline | 10% | 10% | 10% | 10% |
| ethyl acetate | 49.95% | 49.5% | 49% | 50% |
| polymer | polyacrylic acid polymer, 40% | silicone polymer, 40% | polyacrylic acid polymer, 20%, silicone polymer, 20% | polyacrylic acid polymer, 20%, silicone polymer, 20% |
| antioxidant | ascorbyl palmitate, 0.05% | ascorbyl palmitate, 0.5% | ascorbyl palmitate, 1% | — |

Preparation method: rasagiline (free base), the polymer and/or the antioxidant were added to ethyl acetate and mixed to get a sticky matrix. The matrix was coated on a 75 nm thin transparent PET layer (protective layer) to form a 0.2 mm thick film. After being oven-dried at 60° C. for 5 minutes, the film was covered with a back lining made of polyethylene and was transferred, and then the patch was punched or cut into final sheets.

Prior to application to the skin, the protective layer is removed.

The compositions according to the present invention provided a more stable release system (patch) at high temperature. After being stored at 60° C. for 10 days, the content of the related substances of the composition according to the present invention was less than 5%, while that of the related substances of the composition without the antioxidant was greater than 5%, the content of the related substances of the composition according to the present invention was less than 5%, while that of the related substances of the composition without the antioxidant was greater than 5%. The results were shown in Table 8 below.

TABLE 8 content of the related substances of the composition according to Example 3

| storage conditions | content of the related substances of Composition 3-1 | content of the related substances of Composition 3-2 | content of the related substances of Composition 3-3 | content of the related substances of Composition 3-4 |
|---|---|---|---|---|
| 0 day | 0.12% | 0.14% | 0.12% | 0.17% |
| 60° C., 5 days | 1.54% | 0.99% | 0.42% | 3.56% |
| 60° C., 10 days | 3.40% | 1.91% | 0.88% | 12.27% |

A 10 cm² of the patch was attached to the skin of the chest of a human being, and the patches could maintain sufficient adhesion and no falling-off or shift occurred within 3 consecutive days.

EXAMPLE 4

A Transdermal Gel Comprising Rasagiline and Tocopherol as an Antioxidant

TABLE 9

The formula of the composition for a transdermal gel comprising rasagiline and tocopherol as an antioxidant

|  | Composition 4-1 | Composition 4-2 | Composition 4-3 | Composition 4-4 |
|---|---|---|---|---|
| rasagiline | 10% | 10% | 10% | 10% |
| ethanol | 30% | 30% | 30% | 30% |
| water | 58.95% | 51.5% | 58% | 59% |
| polymer | Carbomer 940, 1% | polyvinyl alcohol, 8% | carboxymethyl cellulose sodium, 1% | carboxymethyl cellulose sodium, 1% |
| anti-oxidant | tocopherol, 0.05% | tocopherol, 0.5% | tocopherol, 1% | — |

Preparation method: rasagiline, the polymer and/or the antioxidant were added to ethanol and water, and then stirred. After the polymer was completely swelled, the gel was thus obtained and filled in an ointment tube, and then sealed. The preparation process of the gel was much simpler than that of the patch. When being used, an appropriate amount of the gel was extruded from the ointment tube and applied to skin.

The compositions according to the present invention provide a more stable system at high temperature. After being stored at 60° C. for 10 days, the content of the related substances of the composition according to the present invention was less than 5%, while that of the related substances of the composition without the antioxidant was greater than 5%. The results were shown in Table 10.

TABLE 10 content of the related substances of the composition according to Example 4

| storage conditions | content of the related substances of Composition 4-1 | content of the related substances of Composition 4-2 | content of the related substances of Composition 4-3 | content of the related substances of Composition 4-4 |
|---|---|---|---|---|
| 0 day | 0.04% | 0.04% | 0.03% | 0.05% |
| 60° C., 5 days | 2.04% | 1.03% | 0.77% | 6.75% |
| 60° C., 10 days | 4.48% | 2.71% | 1.79% | 18.93% |

EXAMPLE 5

A Transdermal Gel Comprising Rasagiline and Butylated Hydroxy Toluene as an Antioxidant

TABLE 11

The formula of the composition for a transdermal gel comprising rasagiline and butylated hydroxy toluene as an antioxidant

|  | Composition 5-1 | Composition 5-2 | Composition 5-3 | Composition 5-4 |
|---|---|---|---|---|
| rasagiline | 10% | 10% | 10% | 10% |
| ethanol | 30% | 30% | 30% | 30% |
| water | 58.95% | 51.5% | 58% | 59% |
| polymer | carbomer 940, 1% | polyvinyl alcohol, 8% | carboxymethyl cellulose sodium, 1% | carboxymethyl cellulose sodium, 1% |
| anti-oxidant | butylated hydroxy toluene, 0.05% | butylated hydroxy toluene, 0.5% | butylated hydroxy toluene, 1% | — |

Preparation method: rasagiline, the polymer and/or the antioxidant were added to ethanol and water and then stirred. After the polymer was completely swelled, the gel was thus obtained and filled in an ointment tube, and then sealed. The preparation process of the gel was much simpler than that of the patch. When being used, an appropriate amount of the gel was extruded from the ointment tube and applied to skin.

The compositions according to the present invention provide a more stable system at high temperature. After being stored at 60° C. for 10 days, the content of the related substances of the composition according to the present invention was less than 4%, while that of the related substances of the composition without the antioxidant was greater than 5%. The results were shown in Table 12.

TABLE 12 content of the related substances of the composition according to Example 5

| storage conditions | content of the related substances of Composition 5-1 | content of the related substances of Composition 5-2 | content of the related substances of Composition 5-3 | content of the related substances of Composition 5-4 |
|---|---|---|---|---|
| 0 day | 0.04% | 0.04% | 0.04% | 0.05% |
| 60° C., 5 days | 1.52% | 0.73% | 0.35% | 6.75% |
| 60° C., 10 days | 3.18% | 2.09% | 1.00% | 18.93% |

EXAMPLE 6

A Transdermal Ointment Comprising Rasagiline and an Antioxidant

TABLE 13

The formula of the composition for a transdermal ointment comprising rasagiline and an antioxidant

|  | Composition 6-1 | Composition 6-2 | Composition 6-3 | Composition 6-4 |
|---|---|---|---|---|
| rasagiline | 10% | 10% | 10% | 10% |
| lanolin | 10% | 10% | 10% | 10% |
| liquid paraffin | 10% | 10% | 10% | 10% |
| petrolatum | 69.5% | 69.5% | 69.5% | 69.5% |
| antioxidant | tocopherol, 0.5% | butylated hydroxy toluene, 0.05% | ascorbyl palmitate, 1% | — |

Preparation method: rasagiline and the antioxidant were added to a mixture consisting of lanolin, liquid paraffin and petrolatum. The resulting mixture was grinded into a fine paste, then screened through a 100 mesh sieve, and filled in an ointment tube, and then sealed. When being used, an appropriate amount of the ointment was extruded from the ointment tube and applied to skin.

The compositions according to the present invention provide a more stable system at high temperature. After being stored at 60° C. for 10 days, the content of the related substances of the composition according to the present invention was less than 3%, while that of the related substances of the composition without the antioxidant was greater than 5%, the content of the related substances of the composition according to the present invention was less than 5%, while that of the related substances of the composition without the antioxidant was greater than 5%. The results were shown in Table 14 below.

TABLE 14 content of the related substances of the composition according to Example 6

| storage conditions | content of the related substances of Composition 6-1 | content of the related substances of Composition 6-2 | content of the related substances of Composition 6-3 | content of the related substances of Composition 6-4 |
|---|---|---|---|---|
| 0 day | 0.02% | 0.02% | 0.02% | 0.03% |
| 60° C., 5 days | 1.06% | 1.0% | 0.78% | 4.69% |
| 60° C., 10 days | 2.34% | 2.12% | 1.56% | 11.37% |

EXAMPLE 7

A Transdermal Cream Comprising Rasagiline and Tocopherol as an Antioxidant

TABLE 15

The formula of the composition for a transdermal cream comprising rasagiline and tocopherol as an antioxidant

|  | Composition 7-1 | Composition 7-2 | Composition 7-3 | Composition 7-4 |
|---|---|---|---|---|
| active pharmaceutical ingredient | rasagiline, 10% | rasagiline, 10% | rasagiline, 10% | rasagiline, 10% |
| oil phase | stearic acid, 15% liquid paraffin, 6% lanolin, 10% glycerol monostearate, 10% petrolatum, 1% | stearyl alcohol, 22% petrolatum, 25% | cetyl/stearyl alcohol, 15% beewax, 5% lanolin, 10% petrolatum, 5% | cetyl/stearyl alcohol, 15% beewax, 5% lanolin, 10% petrolatum, 5% |
| emulsifier | triethanolamine 4% | sodium dodecyl sulfate, 1.5% | Tween 80, 5% | Tween 80, 5% |
| antioxidant | tocopherol, 0.05% | tocopherol, 0.5% | tocopherol, 1% | — |
| aqueous phase | water, added to 100% | propylene glycol, 12% water, added to 100% | magnesium aluminum silicate, 5% water, added to 100% | magnesium aluminum silicate, 5% water, added to 100% |

Preparation method: tocopherol as an antioxidant and the active pharmaceutical ingredient rasagiline were added to the oil phase and heated to 80° C. to become a liquid. The aqueous phase, the emulsifier and rasagiline were added thereto, stirred and homogenized. After being cooled down, the cream was obtained. The resulting cream was filled in an ointment tube, and then sealed. When being used, an appropriate amount of the cream was extruded from the ointment tube and applied to skin.

The compositions according to the present invention provide a more stable system at high temperature. After being stored at 60° C. for 10 days, the content of the related substances of the composition according to the present invention was less than 5%, while that of the related substances of the composition without the antioxidant was greater than 5%. The results were shown in Table 16 below.

TABLE 16 content of the related substances of the composition according to Example 7

| storage conditions | content of the related substances of Composition 7-1 | content of the related substances of Composition 7-2 | content of the related substances of Composition 7-3 | content of the related substances of Composition 7-4 |
| --- | --- | --- | --- | --- |
| 0 day | 0.53% | 0.31% | 0.19% | 0.78% |
| 60° C., 5 days | 2.98% | 1.80% | 0.93% | 6.71% |
| 60° C., 10 days | 4.58% | 3.04% | 2.76% | 19.52% |

EXAMPLE 8

A Transdermal Cream Comprising Rasagiline and Butylated Hydroxy Toluene as an Antioxidant

TABLE 17

The formula of the composition for a transdermal cream comprising rasagiline and butylated hydroxy toluene as an antioxidant

|  | Composition 8-1 | Composition 8-2 | Composition 8-3 | Composition 8-4 |
| --- | --- | --- | --- | --- |
| active pharmaceutical ingredient | rasagiline, 10% | rasagiline, 10% | rasagiline, 10% | rasagiline, 10% |
| oil phase | stearic acid, 15% liquid paraffin, 6% lanolin, 10% glycerol monostearate, 10% petrolatum, 1% | stearyl alcohol, 22% petrolatum, 25% | cetyl/stearyl alcohol, 15% beewax, 5% lanolin, 10% petrolatum, 5% | cetyl/stearyl alcohol, 15% beewax, 5% lanolin, 10% petrolatum, 5% |
| emulsifier | triethanolamine, 4% | sodium dodecyl sulfate, 1.5% | Tween 80, 5% | Tween 80, 5% |
| antioxidant | butylated hydroxy toluene, 0.05% 0.5% | butylated hydroxy toluene, | butylated hydroxy toluene, 1% | — |
| aqueous phase | water, added to 100% | propylene glycol, 12% water, added to 100% | magnesium aluminum silicate, 5% water, added to 100% | magnesium aluminum silicate, 5% water, added to 100% |

Preparation method: tocopherol and rasagiline were added to the oil phase and heated to 80° C. to become a liquid. The aqueous phase and the emulsifier were added thereto, stirred and homogenized. After being cooled down, the cream was obtained. The resulting cream was filled in an ointment tube, and then sealed. When being used, an appropriate amount of the cream was extruded from the ointment tube and applied to skin.

The compositions according to the present invention provide a more stable system at high temperature. After being stored at 60° C. for 10 days, the content of the related substances of the composition according to the present invention was less than 5%, while that of the related substances of the composition without the antioxidant was greater than 5%. The results were shown in Table 18 below.

TABLE 18 content of the related substances of the composition according to Example 8

| storage conditions | content of the related substances of Composition 8-1 | content of the related substances of Composition 8-2 | content of the related substances of Composition 8-3 | content of the related substances of Composition 8-4 |
| --- | --- | --- | --- | --- |
| 0 day | 0.34% | 0.23% | 0.11% | 0.78% |
| 60° C., 5 days | 2.03% | 0.79% | 0.48% | 6.71% |
| 60° C., 10 days | 4.08% | 1.85% | 1.24% | 19.52% |

EXAMPLE 9

A Transdermal Cataplasm Comprising Rasagiline and Tocopherol as an Antioxidant

TABLE 19

The formula of the composition for a transdermal cataplasm comprising rasagiline and tocopherol as an antioxidant

|  | Composition 9-1 | Composition 9-2 | Composition 9-3 | Composition 9-4 |
| --- | --- | --- | --- | --- |
| active pharmaceutical ingredient | rasagiline, 2% | rasagiline, 2% | rasagiline, 2% | rasagiline, 2% |
| carrier | gelatin, 3% tragacanth, 3% polyethylene glycol 400, 15% polyacrylic acid, 5% glycerol, 15% zinc oxide, 1.5% tartaric acid, 0.5% azone, 2% water, 52.92% | sodium polyacrylate, 5% polyvinyl-pyrrolidone, 2% sodium carboxymethyl cellulose, 3% glycerol, 30% citric acid, 0.5% titanium dioxide, 7% azone, 2% water, 47.42% | arabic gum, 5% tragacanth, 5% glycerol, 30% kaolin, 5% sodium polyacrylate, 6% azone, 2% water, 42.95% citric acid, 0.5% EDTA, 0.05% | gelatin, 3% tragacanth, 3% polyethylene glycol 400, 15% polyacrylic acid, 5% glycerol, 15% zinc oxide, 1.5% tartaric acid, 0.5% azone, 2% water, 52.97% |
| crosslinking agent | aluminum hydroxide, 0.03% | aluminum hydroxide, 0.03% | aluminum chloride, 0.5% | aluminum hydroxide, 0.03% |
| antioxidant | tocopherol, 0.05% | tocopherol, 0.5% | tocopherol, 1% | — |

Preparation method: rasagiline was dissolved in azone and then mixed with the antioxidant, the crosslinking agent and glycerol. The resulting mixture was grinded into a fine paste (A) for use. After the carrier made of the polymer material was swelled in a part of water, zinc oxide (formula 9-1) or titanium dioxide (formula 9-2) or kaolin and EDTA (formula 9-3) was added thereto and grinded into a paste-like mixture (B) for use. A and B were mixed and grinded. Tartaric acid (formula 9-1) dissolved with remaining water and citric acid (formula 9-2, 9-3) dissolved with remaining water were added to the resulting mixture, and grinded into a paste-like mixture. The paste-like mixture was coated on a non-woven fabric (back liner) with a thickness of 1 mm, and covered with paper which surface was treated with silicon (protective layer), and then allowed stand at room temperature for 2 weeks for crosslinking and solidification to get the cataplasm. The cataplasm was punched or cut into final sheets.

Prior to application to the skin, the protective layer was removed.

The compositions according to the present invention provide a more stable system at high temperature. After being stored at 60° C. for 10 days, the content of the related substances of the composition according to the present invention was less than 4%, while that of the related substances of the composition without the antioxidant was greater than 5%. The results were shown in Table 20 below.

TABLE 20 content of the related substances of the composition according to Example 9

| storage conditions | content of the related substances of Composition 9-1 | content of the related substances of Composition 9-2 | content of the related substances of Composition 9-3 | content of the related substances of Composition 9-4 |
| --- | --- | --- | --- | --- |
| 0 day | 0.12% | 0.10% | 0.10% | 0.18% |
| 60° C., 5 days | 1.51% | 0.46% | 0.35% | 4.32% |
| 60° C., 10 days | 3.28% | 1.39% | 1.01% | 17.68% |

EXAMPLE 10

A Transdermal Cataplasm Comprising Rasagiline and Butylated Hydroxy Toluene as an Antioxidant

TABLE 21

The formula of the composition for a transdermal cataplasm comprising rasagiline and butylated hydroxy toluene as an antioxidant

| | Composition 10-1 | Composition 10-2 | Composition 10-3 | Composition 10-4 |
| --- | --- | --- | --- | --- |
| active pharmaceutical ingredient | rasagiline, 2% | rasagiline, 2% | rasagiline, 2% | rasagiline, 2% |
| carrier | gelatin, 3% tragacanth, 3% polyethylene glycol 400, 15% polyacrylic acid, 5% glycerol, 15% zinc oxide, 1.5% tartaric acid, 0.5% azone, 2% water, 52.92% | sodium polyacrylate, 5% polyvinylpyrrolidone, 5% glycerol, 2% sodium carboxymethyl cellulose, 3% glycerol, 30% citric acid, 0.5% titanium dioxide, 7% azone, 2% water, 47.42% | arabic gum, 5% tragacanth, 5% glycerol, 30% kaolin, 5% sodium polyacrylate, 6% azone, 2% water, 42.95% citric acid, 0.5% EDTA, 0.05% | gelatin, 3% tragacanth, 3% polyethylene glycol 400, 15% polyacrylic acid, 5% glycerol, 15% zinc oxide, 1.5% tartaric acid, 0.5% azone, 2% water, 52.97% |
| crosslinking agent | aluminum hydroxide, 0.03% | aluminum hydroxide, 0.03% | aluminum chloride, 0.5% | aluminum hydroxide, 0.03% |
| antioxidant | butylated hydroxy toluene, 0.05% | butylated hydroxy toluene, 0.5% | butylated hydroxy toluene, 1% | — |

Preparation method: rasagiline was dissolved in azone and then mixed with the antioxidant, the crosslinking agent and glycerol. The resulting mixture was grinded into a fine paste (A) for use. After the carrier made of the polymer material was swelled in a part of water, zinc oxide (formula 10-1) or titanium dioxide (formula 10-2) or kaolin and EDTA (formula 10-3) was added thereto and grinded into a paste-like mixture (B) for use. A and B were mixed and grinded. Tartaric acid (formula 10-1) dissolved with remaining water and citric acid (formula 10-2, 10-3) dissolved with remaining water were added to the resulting mixture, and grinded into a paste-like mixture. The paste-like mixture was coated on a non-woven fabric (back liner) to a thickness of 1 mm, and covered with paper which surface was treated with silicon (protective layer), and then allowed stand at room temperature for 2 weeks for crosslinking and solidification to get the cataplasm. The cataplasm was punched or cut into final sheets.

Prior to application to skin, the protective layer was removed.

The compositions according to the present invention provide a more stable system at high temperature. After being stored at 60° C. for 10 days, the content of the related substances of the composition according to the present invention was less than 4%, while that of the related substances of the composition without the antioxidant was greater than 5%. The results were shown in Table 22 below.

TABLE 22 content of the related substances of the composition according to Example 10

| storage conditions | content of the related substances of Composition 10-1 | content of the related substances of Composition 10-2 | content of the related substances of Composition 10-3 | content of the related substances of Composition 10-4 |
| --- | --- | --- | --- | --- |
| 0 day | 0.13% | 0.11% | 0.11% | 0.18% |
| 60° C., 5 days | 1.35% | 0.39% | 0.36% | 4.32% |
| 60° C., 10 days | 3.01% | 1.07% | 1.12% | 17.68% |

EXAMPLE 11

A Film Administered Via Mucosa Comprising Rasagiline and an Antioxidant

TABLE 23

The formula of the composition for a film administered via mucosa comprising Rasagiline and an antioxidant

| | Composition 11-1 | Composition 11-2 | Composition 11-3 | Composition 11-4 |
|---|---|---|---|---|
| active pharmaceutical ingredient | rasagiline, 1% | rasagiline, 1% | rasagiline, 1% | rasagiline, 1% |
| carrier | polyvinyl alcohol, 30% glycerol, 3% titanium dioxide, 1% Tween 80, 5% water, 59.5% | polyvinyl alcohol, 30% glycerol, 3% titanium dioxide, 1% Tween 80, 5% water, 59.95% | polyvinyl alcohol, 30% glycerol, 3% titanium dioxide, 1% Tween 80, 5% water, 59.5% | polyvinyl alcohol, 30% glycerol, 3% titanium dioxide, 1% Tween 80, 5% water, 60% |
| antioxidant | tocopherol, 0.5% | butylated hydroxy toluene, 0.05% | ascorbyl palmitate, 0.5% | — |

Preparation method: polyvinyl alcohol was swelled in an appropriate amount of water, and then heated in water bath to dissolve and a paste slurry of polyvinyl alcohol was obtained. Rasagiline, the antioxidant, glycerol and Tween 80 were dissolved in an appropriate amount of water and added to the paste slurry of polyvinyl alcohol, and mixed well. Distilled water was added to the required amount. The mixture was mixed well. After bubbles were removed, the mixture was made to film and dried.

When being used, a certain size of the film is attached to the oral mucosa.

The compositions according to the present invention provide a more stable system at high temperature. After being stored at 60° C. for 10 days, the content of the related substances of the composition according to the present invention was less than 4%, while that of the related substances of the composition without the antioxidant was greater than 5%. The results were shown in Table 24 below.

TABLE 24 content of the related substances of the composition according to Example 11

| storage conditions | content of the related substances of Composition 11-1 | content of the related substances of Composition 11-2 | content of the related substances of Composition 11-3 | content of the related substances of Composition 11-4 |
|---|---|---|---|---|
| 0 day | 0.07% | 0.04% | 0.05% | 0.07% |
| 60° C., 5 days | 1.63% | 0.95% | 1.72% | 4.47% |
| 60° C., 10 days | 3.79% | 2.61% | 3.88% | 15.33% |

EXAMPLE 12

A Transdermal Spray Comprising Rasagiline and an Antioxidant

TABLE 25

The formula of the composition for a transdermal spray comprising rasagiline and an antioxidant

| | Composition 12-1 | Composition 12-2 | Composition 12-3 | Composition 12-4 |
|---|---|---|---|---|
| active pharmaceutical ingredient | rasagiline, 1% | rasagiline, 1% | rasagiline, 1% | rasagiline, 1% |
| carrier | ethanol, 20% Tween 80, 5% water, 73.95% | ethanol, 20% Tween 80, 5% water, 73% | ethanol, 20% Tween 80, 5% water, 73.5% | ethanol, 20% Tween 80, 5% water, 73.5% |
| antioxidant | tocopherol, 0.05% | butylated hydroxy toluene, 1.0% | ascorbyl palmitate, 0.5% | — |

Preparation method: rasagiline and the antioxidant were dissolved in ethanol to obtain a mixture A. Tween 80 was dissolved in water to obtain a mixture B. The mixture A and B were mixed well and filled to get the spray.

When being used, the medicine liquid is sprayed on the surface of the skin.

The compositions according to the present invention provide a more stable system at high temperature. After being stored at 60° C. for 10 days, the content of the related substances of the composition according to the present invention was less than 5%, while that of the related substances of the composition without the antioxidant was greater than 5%. The results were shown in Table 26 below.

TABLE 26 content of the related substances of the composition according to Example 12

| storage conditions | content of the related substances of Composition 12-1 | content of the related substances of Composition 12-2 | content of the related substances of Composition 12-3 | content of the related substances of Composition 12-4 |
|---|---|---|---|---|
| 0 day | 0.05% | 0.05% | 0.07% | 0.05% |
| 60° C., 5 days | 2.11% | 0.42% | 1.49% | 3.69% |
| 60° C., 10 days | 4.64% | 1.53% | 3.75% | 13.70% |

It could be seen from the examples and the determination result of the related substances described above, after an antioxidant was added, the patch, gel, ointment, cream, cataplasm, film and spray comprising rasagiline exhibited an unexpected thermal stability, which had a great benefit on the storage of the composition. Compared with the systems described in CN101032474 and CN101606923A, these preparations have better stabilities and can be prepared in simpler way. Compared with CN101606923A, these preparations provide better adhesion to the skin.

Especially for the patch, after addition of an antioxidant as a stabilizer, the matrix material is easy to select and is available, which has a better viscosity to skin, and is not easy to fall off, at the same time keeping a high cumulative penetration volume. Furthermore, the pharmaceutical composition of the invention can be manufactured in a reduced cost and simple industrial operation due to the easy selection and availability of raw materials.

The present invention has been described by way of illustration. However, it should be appreciated that the present invention is not merely limited to these specific embodiments. Various modifications or changes to the present invention may be made by those ordinarily skilled in the art, and these modifications and changes will fall within the scope of the present invention.

What is claimed is:

1. A stable rasagiline composition, comprising rasagiline or a pharmaceutically acceptable salt thereof together with a pharmaceutically acceptable antioxidant, wherein the composition is a transdermal preparation.

2. The composition according to claim 1, wherein the amount of the antioxidant is 0.01% to 1% based on the total weight of the composition.

3. The composition according to claim 1, wherein the amount of rasagiline or a pharmaceutically acceptable salt thereof is 0.1% to 40% based on the total weight of the composition.

4. The composition according to claim 1, wherein the antioxidant is one or more selected from the group consisting of tocopherol or an ester thereof, ascorbyl palmitate, ascorbic acid, butylated hydroxyl toluene, butylated hydroxy anisole or propyl gallate, and citric acid or a salt thereof.

5. The composition according to claim 1, wherein the transdermal preparation is a transdermal patch, cataplasm, emulsion, cream, gel or spray.

6. The composition according to claim 1, further comprises one or more excipients selected from the group consisting of polyacrylic acid polymers, silicone polymers, polyvinyl alcohol polymers, polyvinylpyrrolidone polymers, ethylene vinyl acetate copolymers, cellulose polymers, polyethylene glycol polymers, carbomer polymers, polyethyleneoxide polymers, gelatin, alginic acid or a salt thereof, tragacanth, arabic gum, silicone oil, water, ethanol, acetone, propanol, propylene glycol, glycerol, ethyl acetate, cetyl alcohol, stearyl alcohol, stearic acid, paraffin, beeswax, lanolin compounds, magnesium aluminum silicate, kaolin, titanium dioxide, zinc oxide, aluminum hydroxide, aluminum chloride, citric acid, tartaric acid and ethylene diamine tetraacetic acid.

7. The composition according to claim 5, further comprises a transdermal penetration enhancer.

8. The composition according to claim 7, wherein the transdermal penetration enhancer is one or more selected from azone, isopropyl myristate, oleic acid and menthol.

9. A method for treating or preventing diseases, comprising administering the composition according to claim 1.

10. The method according to claim 9, wherein the disease is one or more selected from the group consisting of Parkinson's disease, Alzheimer's disease, depression, hyperkinetic syndrome of childhood, restless legs syndrome, multiple sclerosis and abstinence syndrome.

11. The composition according to claim 1, wherein the antioxidant is one or more selected from the group consisting of ascorbyl palmitate, ascorbic acid, butylated hydroxyl toluene, butylated hydroxy anisole and butylated hydroxy propyl gallate.

12. The composition according to claim 1, wherein the transdermal preparation is a transdermal patch.

* * * * *